United States Patent
Cavaleri

(10) Patent No.: US 10,376,482 B2
(45) Date of Patent: Aug. 13, 2019

(54) BUTYRATE AND BETA-HYDROXYBUTYRATE COMPOSITIONS

(71) Applicant: Franco Cavaleri, Surrey (CA)

(72) Inventor: Franco Cavaleri, Surrey (CA)

( * ) Notice: Subject to any disclaimer, the term of this patent is extended or adjusted under 35 U.S.C. 154(b) by 465 days.

(21) Appl. No.: 15/187,823

(22) Filed: Jun. 21, 2016

(65) Prior Publication Data
US 2017/0290792 A1   Oct. 12, 2017

Related U.S. Application Data

(60) Provisional application No. 62/317,607, filed on Apr. 3, 2016.

(51) Int. Cl.
| | | |
|---|---|---|
| *A61K 31/19* | (2006.01) | |
| *A61K 45/06* | (2006.01) | |
| *A61K 36/82* | (2006.01) | |

(52) U.S. Cl.
CPC .............. *A61K 31/19* (2013.01); *A61K 36/82* (2013.01); *A61K 45/06* (2013.01)

(58) Field of Classification Search
CPC ........ A61K 31/19; A61K 31/31; A61K 45/06; A61K 36/82
See application file for complete search history.

(56) References Cited

PUBLICATIONS

Cavaleri F and Bashar E "Potential Synergies of β-Hydroxybutyrate and Butyrate on the Modulation of Metabolism, Inflammation, Cognition, and General Health" J. Nutrition and Metabolism, vol. 2018, Article ID 7195760, 13 pp.: doi: 10.1155/2018/7195760. (Year: 2018).*

* cited by examiner

*Primary Examiner* — Aaron J Kosar

(57) ABSTRACT

Compositions and methods for providing a person with an exogenous and therapeutically effective supply of ketones are disclosed. The compositions may consist essentially of (a) purified butyrate (or esters or propionate salts thereof) and (b) purified beta-hydroxybutyrate (or esters or propionate salts thereof). The compositions may further include other pharmacologically active agents, such as acetyl-L carnitine, R-alpha lipoic acid, green tea extract, vitamins, and various combinations of such agents. The methods include providing a person with an exogenous supply of ketones, by orally administering a pharmacologic composition, which is effective to deliver 2000-5000 mg of a short chain fatty acid (e.g., butyrate) and 5000-10,000 mg of ketone (e.g., beta-hydroxybutyrate) on a daily basis.

8 Claims, No Drawings

BUTYRATE AND BETA-HYDROXYBUTYRATE COMPOSITIONS

CROSS-REFERENCE TO RELATED APPLICATIONS

This application claims priority to, and incorporates by reference, U.S. provisional patent application Ser. No. 62/317,607, filed on Apr. 3, 2016.

FIELD OF THE INVENTION

The field of the present invention relates to certain compositions that comprise a combination of short chain fatty acids (such as butyrate) and ketones (such as beta-hydroxybutyrate), which provide the various health benefits described herein.

BACKGROUND OF THE INVENTION

Ketones (Background)

It is well understood that dietary restriction in the form of calorie deprivation and/or a low carbohydrate/high fat diet (LCHFD) is conducive to ketogenesis. Although hyperketonemia (>0.5 mmol/L of serum ketones), when induced by such dietary programs, has been shown to produce positive effects on biological markers of insulin resistance, serum glucose stabilization, diabetes, obesity, epilepsy, cognitive deficits, inflammation and even cancer, achievement and sustenance of functional serum ketone levels is a very difficult task. Achieving a state of ketosis requires dedication and sacrifice, while enduring states of malaise during energy substrate transition. For some, the achievement of ketosis is more difficult than for others based on metabolic, genetic, environmental, and lifestyle factors combined.

Sustained ketosis is also a state desired by athletes in pursuit of improved performance, as a function of ketones serving as substrates for mitochondrial ATP generation. Research shows that ketones produce as much as 38% more ATP per unit carbon than glucose as substrates of the TCA cycle. In addition, research shows ATP generation from ketones as substrates in the mitochondria instead of glucose results in fewer free radical by-products. Furthermore, ketones are shown to induce transcription and subsequent synthesis of endogenous antioxidants, thereby priming the generation of intracellular glutathione and other endogenous antioxidants to produce a proactive protection against oxidative stress.

Athletes in ketosis and under physical load are shown to operate at full power output with a lower VO2 max than those utilizing glucose (carbohydrate) as a primary source of ATP. When at elevated serum levels indicative of ketosis, ketones are also known to spare muscle (anticatabolic) when under stress, including stress caused by nutrient deprivation. Although ketosis is a metabolic state that does not fit optimally for everyone who attempts to achieve it, there are pharmacological benefits of ketones, such as beta-hydroxylbutyrate/beta-hydroxybutyrate (BHB) and acetoacetate when they exist in hyperketonemic states. Healthy ketosis is represented by a state where ketones measure in the range 0.4-5.0 mmol/L, while blood sugar remains stable and at around baseline of 4.2-5.0 mmol/L.

Although it is known that ketones serve as substrates for efficient ATP generation, the means by which such ketones also serve as ligands for various receptors, such as hydroxyl carboxylic acid receptors (HCA), are not well understood. BHB is a known HCA2 receptor agonist and, therefore, it is expected to have some neuroprotective activity, vis-à-vis its activity on monocytes and macrophages.

During carbohydrate deprivation, serum glucose declines and the metabolism can shift to fatty acid beta-oxidation and the production of ketones. This is the essence of endogenous ketone induction. Although fatty acids cannot readily cross the blood brain barrier to serve neurons as an energy substrate amid carbohydrate deprivation, ketones are hydrophilic and can cross to serve efficiently as substrates for neuron ATP generation. Ketones can supply in excess of 50% of the brain's energy requirements during periods of glucose scarcity. The scarcity of glucose amid the abundantly available ketone causes cells to increase mitochondrial numbers, induce endogenous antioxidant generation, and activate various other protective mechanisms.

It has further been established that many neurological disorders are associated with impaired mitochondrial activity, compromised mitochondrial numbers, limited endogenous antioxidant status, elevated free radical generation, and oxidation amongst other pathological features and hallmarks. Ketosis has been shown to improve many of these pathological features.

In view of the foregoing, the exogenous supply of ketones may offer a number of pharmacological benefits, including both mental and physical benefits. A daily supply of exogenous ketones would alleviate the stress associated with diet adherence, and would allow for the pharmacological benefits of ketones to continue due to the maintenance of elevated serum ketone levels (despite the temporary or prolonged increment of serum glucose and stored glycogen that may ensue as a function of a meal or few days off a ketogenic cycle). An exogenous supplement of ketones would also provide an immediate and efficient transition back to a ketogenic lifestyle, without the associated energy deficit that is typically associated with the cell-switch-back to serum ketones and fat as an energy (ATP) substrate. Metabolic support during energy substrate scarcity would be another substantial benefit of an exogenous ketone supply, particularly in the context of calorie or carbohydrate deprivation for weight management or therapy of other types. An exogenously supply of ketones would further serve as a bridging energy source during a low-carbohydrate diet and fluctuations in dietary habits, whether those shifts are long-term initiatives or short-term breaks. An exogenous supply of ketones would serve to avert the state of malaise that is often attendant to a calorie/carbohydrate deprived state, and would improve appetite control and support cognitive alertness.

Butyrate (Background)

Short chain fatty acids, also known as volatile fatty acids, are those typically produced by the microbial community of the intestine. These microbes are often referred to as probiotics or microbiota. Such microbes comprise a significant component of the immune system. These symbiotic microbes produce short chain fatty acids from dietary fiber, i.e., fatty acids that serve as signaling ligands for various receptors involved in inflammatory control, including the HCA2 receptor (the above described beta-hydroxybutyrate (ketone) serves as an agonist for such receptor as well).

The short chain fatty acids of the intestinal lumen include most abundantly, butyrate, propionate, and acetate. Research shows that butyrate fed mice remain lean (despite dietary calorie load); avoid metabolic problems; have increased energy expenditure in the form of body heat generation; and tend to have higher physical activity. Butyrate has been shown to lower serum cholesterol in various studies and by as much as 25% in some studies, and reduce serum triglycerides by as much as 50% compared to controls. Butyrate has further been shown to lower fasting insulin by nearly 50%, and increase insulin sensitivity by as much as 300%. Still further, butyrate administration has been shown to improve appetite and food portion control.

Research has further shown that butyrate is a key fuel for epithelial cells of the intestinal tract and that it may improve gut lining integrity. Similar to BHB, butyrate is an inhibitor of HDAC to induce global changes in genetic transcription of genes encoding oxidative stress resistance. This down regulation of gene transcription results in improved protection from free radical damage associated with strained or extreme metabolic conditions (and environmental toxins). This genetic optimization provided by butyrate also includes neuroprotection, similar to that exhibited by BHB.

Still further, lumen butyrate has been shown to directly preserve gut friendly bacteria in the microbiota, while adversely affecting pathogenic bacteria like *Escherichia coli, Salmonella* spp. and *Campylobacter* spp. Passive absorption of water in the colon depends on short chain fatty acid availability. Butyrate has been shown to play a role in healthy peristalsis to help normalize movement in cases of constipation or diarrhea. Butyrate serves to support optimal hydration and optimal bowel elimination function. Butyrate has also been shown to exhibit trophic effects on intestinal cell proliferation, improving villi, and general lining health. In addition, butyrate has been shown to be a potent promoter of intestinal regulatory T cells establishing yet another immune regulating mechanism that promotes better inflammatory control at the mucosal lining. Promotion of gastrointestinal health provides a formidable platform for improved general and systemic health.

To compound the benefits offered by ketosis (as described above), it is known from the literature that butyrate induces FGF21 in serum, liver and adipocytes, which in turn stimulates fatty acid oxidation and hepatic ketone production. This serves as an inducing signal for ketosis, along with butyrate itself, thereby serving as a direct substrate for ketone production and energy generation. In short, butyrate serves as a significant synergistic force for ketosis induction; BHB ligand interactions and pharmacology; and general health, fitness and performance support.

As discussed above, an exogenous supply of ketones, such as BHB, will provide an immediate alternative energy (ATP) source during periods of calorie or carbohydrate deprivation. However, concurrent butyrate supplementation in the form of sodium, calcium or potassium butyrate (or its esters) will prompt the body to induce endogenous ketone synthesis; will serve as a ligand to stimulate receptors that the ketone will act on; will contribute to the improvement of insulin and general metabolic health; will support inflammatory and general immune system health; will improve gastrointestinal health and integrity—all in parallel with the benefits that concurrent supplementation of the sister ketone molecule will provide.

As the following will demonstrate, the compositions and methods of the present invention will be very useful for providing an exogenous supply of ketones, to provide a person with the numerous pharmacologic benefits described herein.

SUMMARY OF THE INVENTION

According to certain aspects of the invention, compositions are provided that include combinations of short chain fatty acids (e.g., butyrate) and ketones (e.g., beta-hydroxybutyrate), and/or derivatives of the foregoing. The compositions of the present invention offer a multitude of benefits and can be used for numerous applications. For example, oral formulations of such compositions may be used for sustaining elevated lumen and serum short chain fatty acid (SCFA) and/or ketone concentrations intended for therapeutic applications, such as body mass alteration, support of insulin activity, and support of cognitive activity (despite probiotic (microbiome) status and diet). More particularly, the compositions of the invention may be useful for treating or preventing obesity, insulin resistance, metabolic syndromes, cognitive deficits, IBS, IBD, epilepsy, atrophy, and catabolism.

The above-mentioned and additional features of the present invention are further illustrated in the Detailed Description contained herein.

DETAILED DESCRIPTION OF THE INVENTION

The following will describe, in detail, several preferred embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used and made without departing from the scope and spirit of the invention.

According to certain preferred embodiments of the present invention, compositions providing a person with an exogenous and therapeutically effective supply of ketones are disclosed. In certain preferred embodiments, the compositions of the present invention may consist essentially of (a) purified butyrate (or esters or propionate salts thereof) and (b) purified beta-hydroxybutyrate (or esters or propionate salts thereof). The invention provides that the compositions may further include other pharmacologically active agents, such as acetyl-L-carnitine, R-alpha lipoic acid, green tea extract, vitamins, and various combinations of such agents.

The invention provides that acetyl-L-carnitine (a source of L-carnitine following administration) has been shown to support cognition and mood; improve Alzheimer's symptoms; and support cardiovascular health. The invention provides that a composition of the invention that includes acetyl-L-carnitine will be designed to support mitochondrial fatty acid oxidation in the context of a low carbohydrate diet and ketosis. The invention provides that R-alpha lipoic acid will serve as an antioxidant and will support insulin sensitivity (i.e., to provide antioxidant protection in fat and water mediums and improve serum glucose clearance to facilitate ketosis and ketone prevalence as an energy substrate). The inclusion of high-epigallocatechin gallate (EGCG) and high-caffeine green tea extract will provide a natural source caffeine to support beta oxidation of fatty acids and ketosis induction; it will supply a significant amount of EGCG for optimal antioxidant support; and it will provide anti-amylase activity to inhibit or slow carbohydrate digestion to result in an impaired glycemic index of and serum contribution by dietary carbohydrate sources, which promotes a ketogenic environment.

According to additional preferred embodiments of the present invention, methods for providing a person with an exogenous and therapeutically effective supply of ketones are disclosed. In certain embodiments, the methods generally include providing a person with an exogenous supply of ketones (or precursors thereof), by orally administering one of the pharmacologic compositions described herein, which is effective to deliver 1000-5000 mg of a short chain fatty acid (e.g., butyrate) and 1000-10,000 mg of ketone (e.g., beta-hydroxybutyrate) or, more preferably, which is effective to deliver 2000-5000 mg of butyrate and 5000-10,000 mg of beta-hydroxybutyrate to a person on a daily basis. As described further below (and in the Examples), such compositions may be preferably delivered to a person in the form of oral capsules or dry powders.

Notwithstanding the preferred embodiments and Examples described herein, the invention provides that the compositions of the present invention may be administered in any desired and effective manner, e.g., as pharmaceutical compositions or nutritional supplements for oral ingestion. More particularly, for example, pharmaceutically acceptable compositions or nutritional supplements of the invention may comprise one or more of the compositions described herein with one or more acceptable carriers. Regardless of the route of administration selected, the compositions may be formulated into acceptable dosage forms by conventional methods known to those of skill in the art. For example, acceptable carriers include, but are not limited to, sugars (e.g., lactose, sucrose, mannitol, and sorbitol), silicon dioxide, starches, cellulose preparations (such as microcrystalline cellulose), calcium phosphates (e.g., dicalcium phosphate, tricalcium phosphate and calcium hydrogen phosphate), sodium citrate, water, aqueous solutions, alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes, paraffins, silicones, talc, silicylate, etc.

Each acceptable carrier used in a pharmaceutical composition or nutritional supplement of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

The pharmaceutical compositions and nutritional supplements of the invention may, optionally, contain additional ingredients and/or materials commonly used in pharmaceutical compositions and/or nutritional supplements. These ingredients and materials include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxy methyl cellulose and sodium carbonate; (5) solution retarding agents, such as paraffin; (6) absorption accelerators, such as quaternary ammonium compounds; (7) wetting agents, such as cetyl alcohol and glycerol monosterate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; (28) vitamins and minerals; (29) proteins that carry therapeutic or nutritional benefits, such as whey protein and other milk-derived proteins; and (30) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Pharmaceutical compositions and nutritional supplements suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, or a paste. These formulations may be prepared by methods known in the art, e.g., by means of conventional pan-coating, mixing, granulation or lyophilization processes.

Solid dosage forms for oral administration (capsules, tablets, pills, powders, granules and the like) may be prepared by mixing the active ingredient(s) with one or more acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as capsules, pills and granules, may optionally be scored or prepared with coatings and shells, such as enteric coatings and other coatings well known in the art. The tablets, and other solid dosage forms, may also be formulated so as to provide slow or controlled release of the active ingredient therein. They may be sterilized by, for example, filtration through a bacteria-retaining filter. These compositions may also optionally contain opacifying agents that release the active ingredient only, or preferentially, in a certain portion of the gastrointestinal tract, optionally, in a delayed manner. The active ingredient can also be in a microencapsulated form.

Liquid dosage forms for oral administration include acceptable emulsions, microemulsions, solutions, suspensions, syrups, and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

EXAMPLES

Example 1

The following Example describes a composition of the present invention, which includes butyrate salts (and/or esters or propionate salts thereof), in combination with beta-hydroxybutyrate salts (and/or esters or propionate salts thereof). In this Example, the target subject will preferably receive, on a daily basis, 1000-5000 mg of a short chain fatty acid (e.g., butyrate) and 1000-10,000 mg of ketone (e.g., beta-hydroxybutyrate)—or, more preferably, 2000-5000 mg of butyrate and 5000-10,000 mg of beta-hydroxybutyrate. The invention provides that additional optimizing ingredients may be included in the formulation. For example, acetyl carnitine may be included, to provide a fatty acid transport mechanism facilitator. In addition, R-alpha lipoic acid may be included to improve insulin efficacy and to drive serum glucose levels down to be conducive to ketogenesis and ketone body prevalence as an ATP substrate.

In the following Example, the invention provides that an approximate 2:1 (butyrate:beta-hydroxybutyrate) ratio may be employed. Alternatively, the invention provides that a 1:1 ratio can also be used, or other ratios that are deemed suitable for the mode of delivery and the body mass of the target subject (person). The following provides an example formulation of the compositions of the present invention, showing a capsule formulation (at 1:1 and 2:1 ratios of butyrate and beta-hydroxybutyrate) and a powder formulation.

Capsules (1:1 butyrate/beta-hydroxybutyrate ratio)

| Component | Amount (mg) |
| --- | --- |
| Butyrate Sodium Salt | 100 |
| Butyrate Calcium Salt | 100 |
| Butyrate Magnesium Salt | 100 |
| Beta Hydroxybutyrate Sodium Salt | 100 |
| Beta Hydroxybutyrate Calcium Salt | 100 |
| Beta Hydroxybutyrate Magnesium Salt | 200 |
| Acetyl-L Carnitine | 70 |
| R alpha lipoic acid | 12 |
| Green Tea Extra (14% Caffeine) | 70 |
| Total per capsule | 852 |

Capsules (2:1 butyrate/beta-hydroxybutyrate ratio)

| Component | Amount (mg) |
| --- | --- |
| Butyrate Sodium Salt | 50 |
| Butyrate Calcium Salt | 50 |
| Butyrate Magnesium Salt | 100 |
| Beta Hydroxybutyrate Sodium Salt | 100 |
| Beta Hydroxybutyrate Calcium Salt | 100 |
| Beta Hydroxybutyrate Magnesium Salt | 200 |
| Acetyl-L Carnitine | 70 |
| R alpha lipoic acid | 12 |
| Green Tea Extra (14% Caffeine) | 70 |
| Total per capsule | 852 |

Powder Pouch/Canister

| Component | Amount (mg) |
| --- | --- |
| Powdered Cream/Butter Powder | 3000 |
| Coconut Fat/Cream Powder | 2000 |
| Butyrate Sodium Salt | 1000 |
| Butyrate Calcium Salt | 1000 |
| Butyrate Magnesium Salt | 1000 |
| Beta Hydroxybutyrate Sodium Salt | 1000 |
| Beta Hydroxybutyrate Calcium Salt | 1000 |
| Beta Hydroxybutyrate Magnesium Salt | 1000 |
| Resistant Starch | 10000 |
| Agave Extract | 2000 |
| Stevia | 90 |
| Berry Flavor | 1000 |
| Vitamin B1 diphosphate | 5 |
| Vitamin B2 Riboflavin | 5 |
| Vitamin B2 Riboflavin 5'-phosphate | 5 |
| Niacin B3 | 10 |
| Niacinaminde B3 | 5 |
| NADH B3 | 5 |
| Vitamin B5 panthenol | 5 |
| Vitamin B6 pyridoxine HCl | 5 |
| Vitamin B6 pyridoxine 5'-phosphate | 5 |
| Vitamin B7 Biotin | 0.5 |
| Vitamin B9 Folic Acid | 1 |
| Vitamin B12 | 1 |
| Inositol | 0.3 |
| Choline Bitartrate | 0.3 |
| Acetyl-L Carnitine | 700 |
| R alpha lipoic acid | 12 |
| Green Tea Extra (14% Caff total) | 70 |
| Total | 24,843 |

Example 2

The following Example describes another composition of the present invention, which includes butyrate salts (and/or esters or propionate salts thereof), in combination with beta-hydroxybutyrate salts (and/or esters or propionate salts thereof). In this Example, the composition was formulated as individual capsules, which comprised the components set forth in the table below.

| Component | Amount (mg)/% Total |
| --- | --- |
| Calcium Butyrate Powder | 50 (8.0%) |
| Magnesium Butyrate Powder | 150 (23.8%) |
| Sodium Beta Hydroxybutyrate Powder | 102 (16.2%) |
| Magnesium Beta Hydroxybutyrate Powder | 306 (48.6%) |
| Other (Magnesium Stearate; Silicon Dioxide; Capsule Vegetable Oil) | 22 (3.4%) |
| Total | 630 (100%) |

Example 3

The capsule described in Example 2 was administered to a male subject, 49 years of age with a body weight of 190 pounds, who exhibited above-average fitness. The subject was administered a total of five (5) capsules at time=0 (following approximately four (4) hours of fasting), and the subject's serum glucose and serum ketone levels were subsequently measured at the time points listed in the table below.

| Time (Minutes/Post-Admin) | 0 | 15 | 30 | 45 | 60 |
|---|---|---|---|---|---|
| Serum Glucose (mM/L) | 4.3 | 4.1 | 4.2 | 4.6 | 4.7 |
| Serum Ketone (mM/L) | 0.25 | 0.4 | 0.4 | 0.5 | 0.4 |

Example 4

In this Example, the capsule described in Example 2 was administered to the male subject described in Example 3. The subject was administered a total of eight (8) capsules at time=0 (following approximately twelve (12) hours of fasting), and the subject's serum glucose and serum ketone levels were subsequently measured at the time points listed in the table below.

| Time (Minutes/Post-Admin) | 0 | 15 | 45 | 60 | 75 | 90 | 105 |
|---|---|---|---|---|---|---|---|
| Serum Glucose (mM/L) | 4.7 | 5.3 | 5.6 | 5.4 | 5.6 | 6.0 | 4.9 |
| Serum Ketone (mM/L) | 0.2 | 0.2 | 0.4 | 0.4 | 0.4 | 0.2 | 0.2 |

Example 5

In this Example, the capsule described in Example 2 was administered to the male subject described in Example 3. The subject was administered a total of six (6) capsules at time=0 (following approximately three (3) hours of fasting), and the subject's serum glucose and serum ketone levels were subsequently measured at the time points listed in the table below.

| Time (Minutes/Post-Admin) | 0 | 15 | 30 | 45 | 60 | 75 |
|---|---|---|---|---|---|---|
| Serum Glucose (mM/L) | 4.5 | 4.1 | 4.8 | 4.9 | 4.2 | 4.2 |
| Serum Ketone (mM/L) | 0.2 | 0.2 | 0.3 | 0.4 | 0.3 | 0.2 |

As shown in Examples 3-5, a composition of the present invention was effective to induce healthy ketosis in a subject (represented by a state where ketones are elevated), while maintaining a relatively stable blood sugar level.

The many aspects and benefits of the invention are apparent from the detailed description, and thus, it is intended for the following claims to cover all such aspects and benefits of the invention that fall within the scope and spirit of the invention. In addition, because numerous modifications and variations will be obvious and readily occur to those skilled in the art, the claims should not be construed to limit the invention to the exact construction and operation illustrated and described herein. Accordingly, all suitable modifications and equivalents should be understood to fall within the scope of the invention as claimed herein.

What is claimed is:

1. A composition consisting essentially of:
   (a) purified butyrate or esters or propionate salts thereof, wherein the purified butyrate includes a butyrate sodium salt, a butyrate calcium salt, and a butyrate magnesium salt; and
   (b) purified beta-hydroxybutyrate or esters or propionate salts thereof, wherein the purified beta-hydroxybutyrate includes a beta-hydroxybutyrate sodium salt, a beta-hydroxybutyrate calcium salt, and a beta-hydroxybutyrate magnesium salt, wherein (i) the total purified butyrate to total purified beta-hydroxybutyrate ratio is about 2:1 and (ii) the composition is packaged within an oral capsule or in powdered form.

2. The composition of claim 1, which further comprises an agent selected from the group consisting of acetyl-L carnitine, R-alpha lipoic acid, and green tea extract.

3. The composition of claim 1, wherein the total purified butyrate to total purified beta-hydroxybutyrate ratio is about 1:1.

4. The composition of claim 1, which further comprises one or more vitamins.

5. A composition consisting essentially of:
   (a) purified butyrate or esters or propionate salts thereof, wherein the purified butyrate includes a butyrate sodium salt, a butyrate calcium salt, or a butyrate magnesium salt; and
   (b) purified beta-hydroxybutyrate or esters or propionate salts thereof, wherein the purified beta-hydroxybutyrate includes a beta-hydroxybutyrate sodium salt, a beta-hydroxybutyrate calcium salt, or a beta-hydroxybutyrate magnesium salt, wherein the composition is packaged in a form selected from the group consisting of (i) an oral capsule, (ii) in powdered form, (iii) in an aqueous or non-aqueous liquid, (iv) in an oil-in-water or water-in-oil emulsion, (v) in an elixir or syrup, or (vi) in a paste.

6. The composition of claim 5, which further comprises an agent selected from the group consisting of acetyl-L carnitine, R-alpha lipoic acid, and green tea extract.

7. The composition of claim 5, which further comprises one or more vitamins.

8. The composition of claim 5, which further comprises one or more preservatives.

* * * * *